(12) United States Patent
Marczyk et al.

(10) Patent No.: US 9,687,227 B2
(45) Date of Patent: Jun. 27, 2017

(54) APPARATUS AND METHOD OF FORMING BARBS ON A SUTURE

(75) Inventors: Stanislaw Marczyk, Stratford, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/417,612

(22) Filed: Mar. 12, 2012

(65) Prior Publication Data

US 2012/0277793 A1    Nov. 1, 2012

Related U.S. Application Data

(60) Provisional application No. 61/480,658, filed on Apr. 29, 2011.

(51) Int. Cl.
*A61B 17/04* (2006.01)
*A61B 17/06* (2006.01)
*A61B 17/00* (2006.01)

(52) U.S. Cl.
CPC ............ *A61B 17/06166* (2013.01); *A61B 2017/00526* (2013.01); *A61B 2017/06176* (2013.01); *Y10T 83/02* (2015.04)

(58) Field of Classification Search
CPC ................................................ A61B 17/06166
USPC ............. 606/228, 139, 148; 425/76; 83/861
See application file for complete search history.

(56) References Cited

U.S. PATENT DOCUMENTS

| | | | |
|---|---|---|---|
| 6,848,152 B2 | 2/2005 | Genova et al. | |
| 7,225,512 B2 | 6/2007 | Genova et al. | |
| 7,913,365 B2 | 3/2011 | Genova et al. | |
| 7,996,967 B2 | 8/2011 | Genova et al. | |
| 7,996,968 B2 | 8/2011 | Genova et al. | |
| 8,011,072 B2 | 9/2011 | Genova et al. | |
| 8,015,678 B2 | 9/2011 | Genova et al. | |
| 8,020,263 B2 | 9/2011 | Genova et al. | |
| 8,028,387 B2 | 10/2011 | Genova et al. | |
| 8,028,388 B2 | 10/2011 | Genova et al. | |
| 8,032,996 B2 | 10/2011 | Trull et al. | |
| 8,100,940 B2 | 1/2012 | Leung et al. | |
| 8,118,834 B1 | 2/2012 | Goraltchouk et al. | |
| 8,161,618 B2 | 4/2012 | Maiorino et al. | |

(Continued)

FOREIGN PATENT DOCUMENTS

WO    WO2007/131019 A2    11/2007
WO    WO2008/042992 A2    4/2008

(Continued)

OTHER PUBLICATIONS

European Search Report EP12165938 dated Jan. 22, 2013.
European Search Report EP 12 16 5912 dated Jul. 18, 2012.
European Search Report EP 12 16 9370 dated Sep. 12, 2012.

*Primary Examiner* — Gregory Anderson
*Assistant Examiner* — Sarah Simpson

(57) ABSTRACT

A barbed suture is provided. The barbed suture includes an elongate body and at least one barb extending from the elongate body. The elongate body defines a recess adjacent the at least one barb. Also provided is a method of making a barbed suture. The method includes the steps of providing a suture nest and a punch apparatus configured for operable engagement with the suture nest, loading a suture through the suture nest, engaging the punch apparatus with the suture nest, and disengaging the punch apparatus with the suture nest.

22 Claims, 13 Drawing Sheets

(56) References Cited

U.S. PATENT DOCUMENTS

| | | | |
|---|---|---|---|
| 8,192,462 B2 | 6/2012 | Sulamanidze | |
| 8,216,273 B1 * | 7/2012 | Goraltchouk et al. | 606/228 |
| 8,216,497 B2 * | 7/2012 | Lindh et al. | 264/153 |
| 8,454,653 B2 * | 6/2013 | Hadba et al. | 606/228 |
| 2003/0041426 A1 | 3/2003 | Genova et al. | |
| 2003/0149447 A1 | 8/2003 | Morency | |
| 2004/0060410 A1 | 4/2004 | Leung et al. | |
| 2004/0226427 A1 | 11/2004 | Trull et al. | |
| 2004/0237736 A1 | 12/2004 | Genova et al. | |
| 2005/0234480 A1 | 10/2005 | Nam et al. | |
| 2007/0005109 A1 | 1/2007 | Popadiuk et al. | |
| 2007/0065663 A1 * | 3/2007 | Trull | A61B 17/06166 |
| | | | 428/357 |
| 2007/0187861 A1 * | 8/2007 | Genova et al. | 264/165 |
| 2007/0257395 A1 | 11/2007 | Lindh | |
| 2008/0082113 A1 | 4/2008 | Bishop | |
| 2008/0195147 A1 | 8/2008 | Stopek | |
| 2008/0221618 A1 | 9/2008 | Chen | |
| 2008/0281357 A1 | 11/2008 | Sung | |
| 2008/0312688 A1 | 12/2008 | Nawrocki | |
| 2009/0012560 A1 * | 1/2009 | Hunter | A61B 17/06166 |
| | | | 606/228 |
| 2009/0076543 A1 | 3/2009 | Maiorino et al. | |
| 2009/0140012 A1 | 6/2009 | Greer, Jr. | |
| 2009/0248066 A1 | 10/2009 | Wilkie | |
| 2009/0287245 A1 | 11/2009 | Ostrovsky | |
| 2010/0023055 A1 | 1/2010 | Rousseau | |
| 2010/0084780 A1 | 4/2010 | Lindh, Sr. | |
| 2010/0146770 A1 | 6/2010 | Morency et al. | |
| 2010/0275750 A1 | 11/2010 | Maiorino et al. | |
| 2010/0313729 A1 | 12/2010 | Genova et al. | |
| 2011/0046669 A1 | 2/2011 | Goraltchouk | |
| 2011/0125188 A1 | 5/2011 | Goraltchouk | |
| 2011/0282384 A1 | 11/2011 | Odermatt et al. | |
| 2011/0288583 A1 | 11/2011 | Goraltchouk | |
| 2012/0046675 A1 | 2/2012 | Bishop | |
| 2012/0104644 A1 | 5/2012 | Lauria | |
| 2012/0118123 A1 | 5/2012 | Maiorino et al. | |
| 2012/0132054 A1 | 5/2012 | Maiorino et al. | |

FOREIGN PATENT DOCUMENTS

| | | |
|---|---|---|
| WO | WO2008/112417 A2 | 9/2008 |
| WO | WO2008/141034 A1 | 11/2008 |
| WO | WO2008/157142 A2 | 12/2008 |
| WO | WO2009/020795 | 2/2009 |
| WO | WO 2009/105663 A2 | 8/2009 |
| WO | WO 2009/129251 A2 | 10/2009 |
| WO | WO2009/132284 A2 | 10/2009 |
| WO | WO2009/140012 A1 | 11/2009 |

* cited by examiner

APPARATUS AND METHOD OF FORMING BARBS ON A SUTURE

CROSS-REFERENCE TO RELATED APPLICATION

The present application claims the benefit of and priority to U.S. Provisional Application Ser. No. 61/480,658, filed Apr. 29, 2011, the content of which is incorporated by reference herein in its entirety.

BACKGROUND

Technical Field

The present disclosure relates to apparatus and methods for forming barbs on sutures. More particularly, the present disclosure relates to apparatus and methods of forming barbs on sutures using heat staking.

Background of Related Art

Barbed sutures are generally made of the same materials as conventional sutures and offer several advantages for closing wounds compared with conventional sutures. A barbed suture includes an elongate body that has one or more spaced barbs which project outward from the surface of the suture body along the body length. The barbs are arranged to allow passage of the barbed suture in one direction through tissue but resist movement of the barbed suture in the opposite direction. Thus, one advantage of barbed sutures has been the provision of a non-slip attribute.

Barbed sutures are used in countless procedures. The number of barbs called for on a particular suture may be influenced by the size of the wound and the strength required to hold the wound closed. Like a conventional suture, a barbed suture may be inserted into tissue using a surgical needle.

In some circumstances, a specific configuration of barbs on the exterior surface of the suture is preferred to achieve optimal wound closure holding for the particular wound. However, in other circumstances, where the wound or tissue repair needed is relatively small, a reduced number of barbs may be desired. In other circumstances, a bi-directional barbed suture is desirable where the barbs over a portion of the suture permit passing of the suture in one direction and barbs over another portion of the suture permit passing of the suture in a second direction to perform a tight closing stitch.

Various methods of forming barbs on sutures have been proposed such as mechanical cutting, laser cutting, injection molding, extrusion and the like. However, such methods may be difficult or costly to achieve the desired result with respect to getting the arrangement of barbs in a configuration needed for the appropriate procedure and for doing so in an efficient cost effective manner.

Accordingly, there is a continuing need for methods of forming barbs on a suture that are less difficult, more effective and/or economical. There is also a continuing need for methods which are able to vary the size, the number, the location and/or the depth of the barbs.

SUMMARY

A system for forming one or more barbs on a length of suture is provided. The system includes a suture nest and a punch apparatus. The suture nest defines a longitudinal passage configured for receipt of a length of suture. The suture nest includes at least one recess formed along the longitudinal passage and at least one opening corresponding to the at least one recess. The punch apparatus includes at least one punch member corresponding to the at least one opening in the suture nest. The at least one punch member is configured to be selectively received within the at least one opening in the suture nest.

In one embodiment, the suture nest includes a plurality of recesses and a plurality of corresponding openings. The punch apparatus may include a plurality of punch members corresponding to the plurality of openings in the suture nest. At least one of the punch apparatus and the nest may be selectively movable relative to the other. The suture nest may include first and second nest halves and at least one recess may be formed in one of the first and second nest halves. At least one opening corresponding to the at least one recess may be formed on the other of the first and second nest halves.

A suture forming nest is also provided. The suture forming nest includes a first nest half defining a first longitudinal groove and a second nest half defining a second longitudinal groove corresponding to the first longitudinal groove. The first nest half further defines at least a first recess formed along the longitudinal groove. The second nest half further defines at least a first opening extending therethrough corresponding to the at least first recess of the first nest half.

In one embodiment, the first and second nest halves each include an inner surface configured to be in contact during a suture forming process. The first and second longitudinal grooves may form a longitudinal passage for receiving a suture when the first and second inner surfaces of the first and second nest halves are in contact. The first nest half may include a plurality of recesses formed along the first longitudinal groove. The plurality of recesses may be formed on alternating sides of the first longitudinal groove. The second nest half may include a plurality of openings formed along the first longitudinal groove. The plurality of openings may be formed on alternating sides of the second longitudinal groove. The at least one recess may form one of a pointed barb and a rounded barb. The second nest half may be configured to engage a punch.

Also provided is a punch device for use with a suture forming nest. The apparatus includes a base and at least one punch assembly extending from the base. The at least one punch assembly includes a base member and a punch member. The punch member may be configured for reception within an opening of the suture nest. The base member may be selectively extendable relative to the base and/or the base member. The distal end of the punch member may be configured to engage a suture. The punch device may further include a mechanism for heating the at least one punch member.

Additionally, a barbed suture is provided. The barbed suture includes an elongate body and at least one barb extending from the elongate body, wherein the elongate body defines a recess adjacent the at least one barb. In one embodiment, the elongate body includes a plurality of barbs. The barbed suture may further include one or more ridges extending about the recess defined in the elongate body. The plurality of ridges corresponds to each of the plurality of barbs. The recesses adjacent the at least one barb may be oriented in the same direction as the at least one barb. The recess may be substantially oval.

A method of making a barbed suture is also provided. The method includes the steps of providing a suture nest and a punch apparatus configured for operable engagement with the suture nest, loading a suture through the suture nest, engaging the punch apparatus with the suture nest, and disengaging the punch apparatus with the suture nest. The suture nest may include first and second suture halves. The first nest half may define a first longitudinal groove and at least a first recess formed along the longitudinal groove. The second nest half may define a second longitudinal groove corresponding to the first longitudinal groove and at least a first opening extending therethrough corresponding to the at least first recess of the first nest half. The first and second longitudinal grooves may form an elongate passage through the nest when the first and second nest halves are engaged.

BRIEF DESCRIPTION OF THE DRAWINGS

Various embodiments of the present disclosure will be described herein below with reference to the figures wherein.

DETAILED DESCRIPTION

Figure 1A:
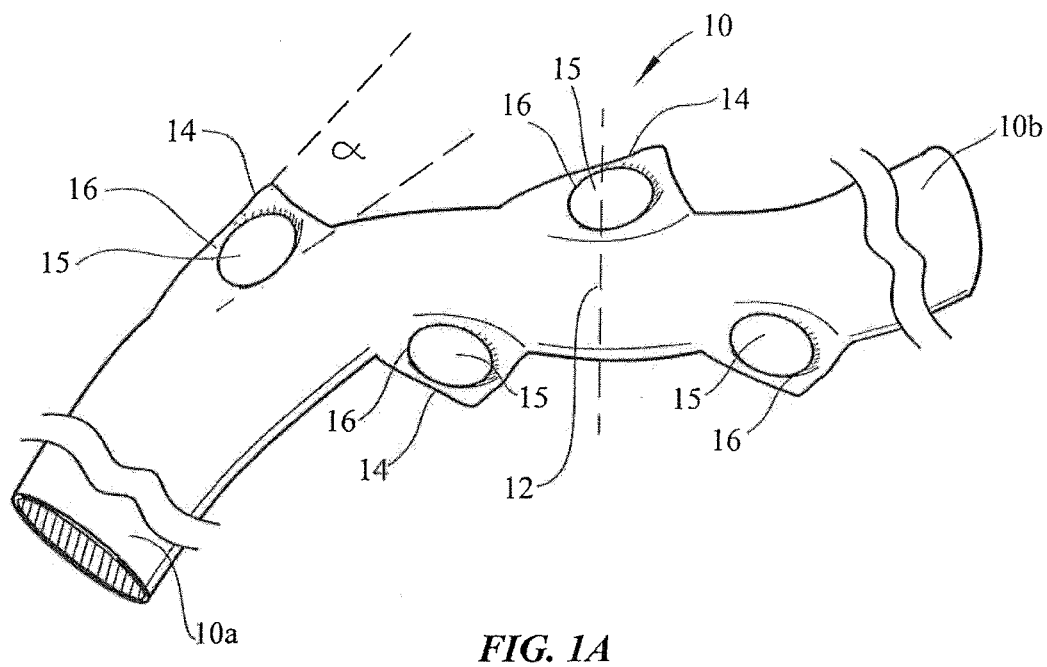
FIG. 1A is a perspective view of an embodiment of a barbed suture formed of a monofilament thread in accordance with the present disclosure.
Figure 1B:
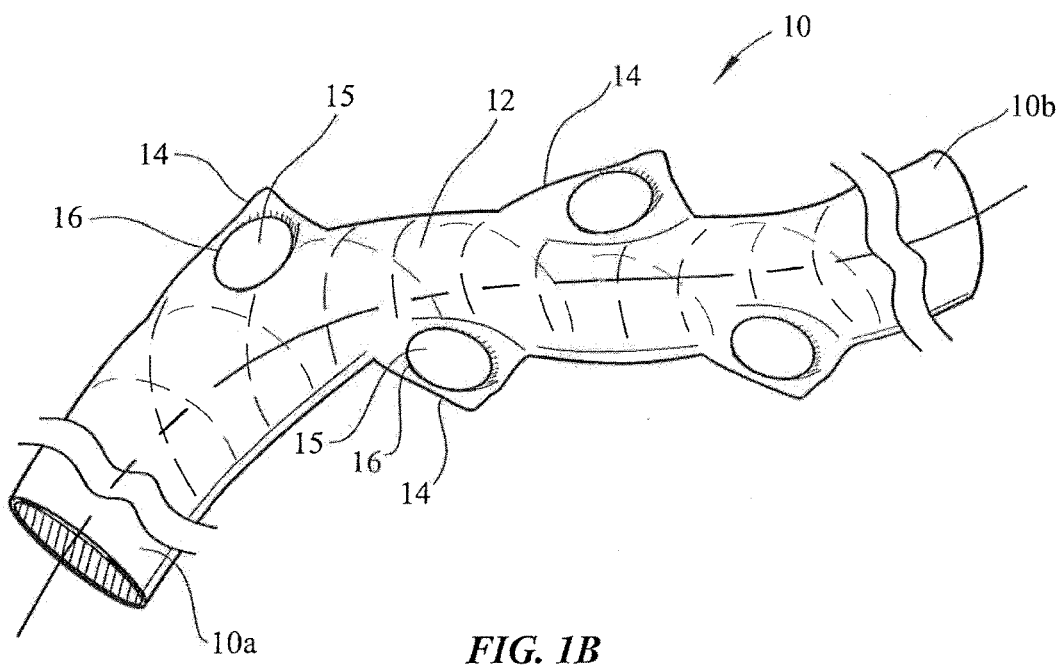
FIG. 1B is a perspective view of another embodiment of a barbed suture formed of a multifilament braided thread in accordance with the present disclosure.

Disclosed herein are an apparatus, system and method for forming a suture having at least one barb formed along the length thereof. Referring now in detail to the drawings in which like reference numerals are applied to like elements in the various views, FIGS. 1A and 1B illustrate a length of suture 10 having an elongate body 12 and a plurality of barbs 14 formed therefrom. Suture 10 has a proximal end 10a and distal end 10b. Either or both of proximal and distal ends 10a, 10b may include a needle (not shown). As shown, barbs 14 are formed projecting outward from elongate body 12 of suture 10 in a first direction, however, it is envisioned that barbs 14 may project outwardly in a first direction along a first portion of suture 10 and a second length of barbs 14 may project outwardly in a second direction along a second portion of suture 10, thereby forming a bi-directional barbed suture.

Figure 1C:
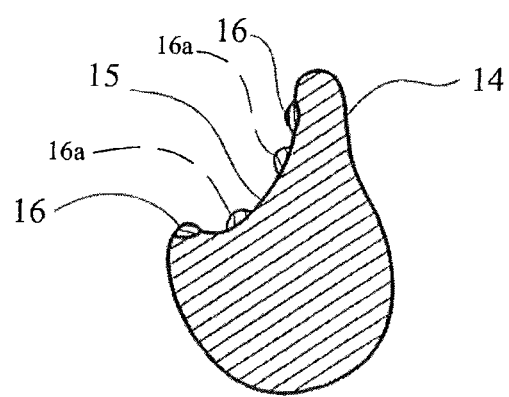
FIG. 1C is a cross-sectional view of the barbed suture of FIG. 1A.

With reference still to FIGS. 1A and 1B, barbs 14 form an angle "α" (FIG. 1A) of less than ninety degrees (90°) between barbs 14 and elongate body 12. Each of barbs 14 includes a cavity or recess 15 which is at least partially disposed along elongate body 12. As shown, each recess 15 is defined by a ridge 16 (FIG. 1C). Ridges 16 are formed from a portion of elongate body 12 and have an increased thickness and/or density. Ridges 16 are created as part of the barb forming process. Although shown including ridges 16, it is envisioned that elongate body 12 may define one or more recesses 15 formed without ridges 16. Alternatively, it is envisioned that elongate body 12 may define a recess formed with multiple ridges 16, 16a. (See FIG. 1C, shown in phantom). Recesses 15 and/or ridges 16 may be configured to add structural strength to barbs 14 and/or elongate body 12. As seen in FIGS. 1A and 1B, recesses 15 are oriented in the same direction as barbs 14.

As shown in FIG. 1A, suture 10 is formed of a monofilament thread. With reference to FIG. 1B, as shown, suture 10 is formed of braided threads. The braiding may be done by any method within the purview of those skilled in the art. The filaments and/or fibers used for forming suture 10 may be formed using any technique within the purview of those skilled in the art, such as, for example, extrusion and/or molding. In some embodiments, the suture may include a yarn made of more than one filament. The filament or filaments may contain multiple strands of the same or different materials. Where suture 10 is made of multiple filaments, suture 10 may be made using any known technique such as, for example, braiding, weaving or knitting. The filaments may also be combined to produce a nonwoven suture. The filaments themselves may be drawn, oriented, crinkled, twisted, commingled or air entangled to form yarns as part of the suture forming process. As will become apparent from the following disclosure, certain aspects of the present disclosure are especially well suited for use with braided and/or multifilament sutures as the barb forming process may operate to join or secure the multiple threads with each other.

Suture 10 may be formed of degradable materials, non-degradable materials, and combinations thereof. More particularly, suture 10 may be formed of a degradable material selected from the group consisting of polyesters, polyorthoesters, polymer drugs, polyhydroxybutyrates, proteins, carbonates, homopolymers thereof, copolymers thereof, and combinations thereof. In other embodiments, suitable degradable materials which may be utilized to form suture 10 include natural collagenous materials or synthetic resins.

Suitable non-degradable materials which may be utilized to form suture 10 include polyolefins, such as polyethylene and polypropylene; copolymers of polyethylene and polypropylene, and blends of polyethylene and polypropylene; polyamides (such as nylon); polyamines; polyimines; polyesters such as polyethylene terephthalate; polytetrafluoroethylene; polyether-esters such as polybutester; polytetramethylene ether glycol; 1,4-butanediol; polyurethanes; and combinations thereof. The polypropylene may be isotactic polypropylene or a mixture of isotactic and syndiotactic or atactic polypropylene.

Figure 2:
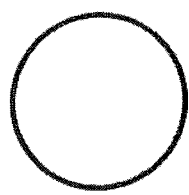
FIGS. 2A-2G are ends views of sutures having alternative cross-sectional geometries, including circular (FIG. 2A), elliptical (FIG. 2B), square (FIG. 2C), star-shaped (FIG. 2D), octagonal (FIG. 2E), rectangular (FIG. 2F), and planar (FIG. 2G)
Figure 2:
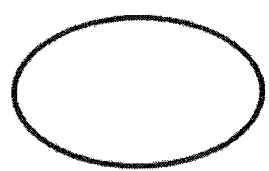
Figure 2:
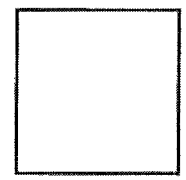
Figure 2:
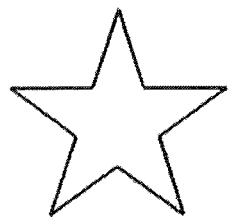
Figure 2:
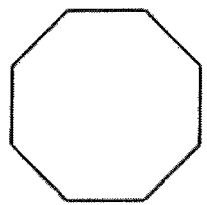
Figure 2:
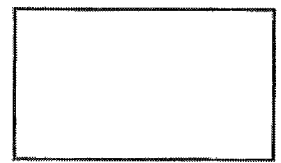
Figure 2:

As shown in FIGS. 1A and 1B, suture 10 is circular in cross-sectional geometry, however, the cross-sectional geometry of suture 10 may be of any suitable shape. For example, with reference to FIGS. 2A-2G, the cross-sectional geometry of suture 10 may include, circular (FIG. 2A), elliptical (FIG. 2B), square (FIG. 2C), star-shaped (FIG. 2D), octagonal (FIG. 2E), rectangular (FIG. 2F), and planar (FIG. 2G).

Figure 3:
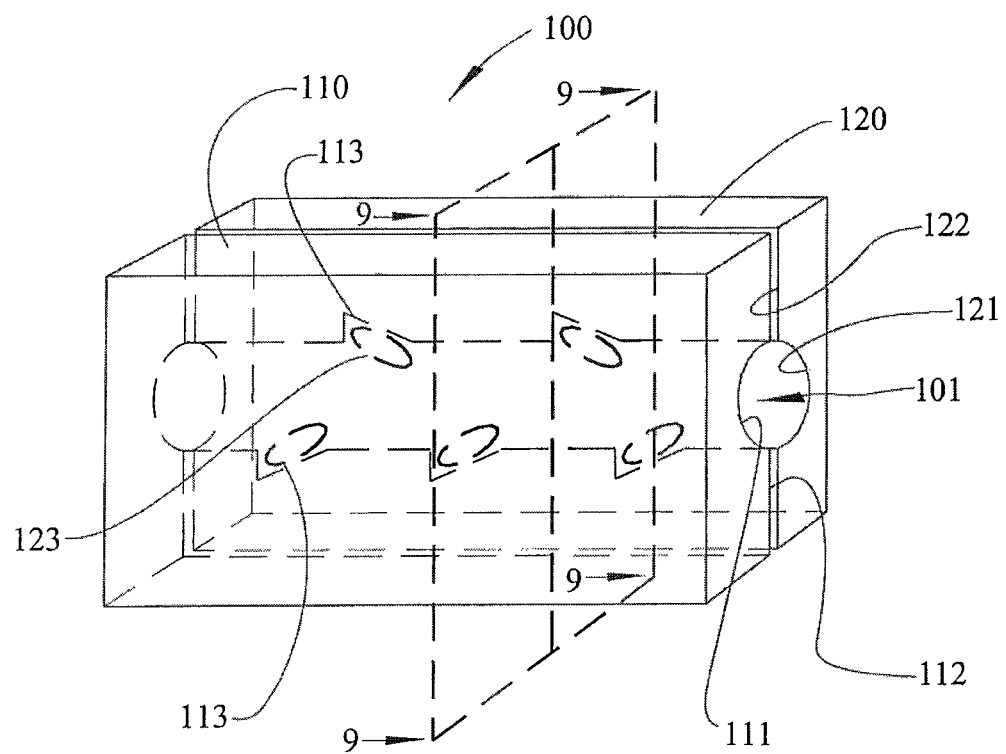
FIG. 3 is a perspective view of a barbed suture forming nest according to an embodiment of the present disclosure.

With reference now to FIG. 3, an embodiment of an apparatus for forming barbs 14 on suture 10 (FIGS. 1A and 1B) is shown generally as suture forming nest 100. Suture forming nest 100 includes first and second nest halves 110, 120. First and second nest halves 110, 120 cooperate to form a cavity 101 configured for receipt of a length of suture 10 therein.

Figure 4A:
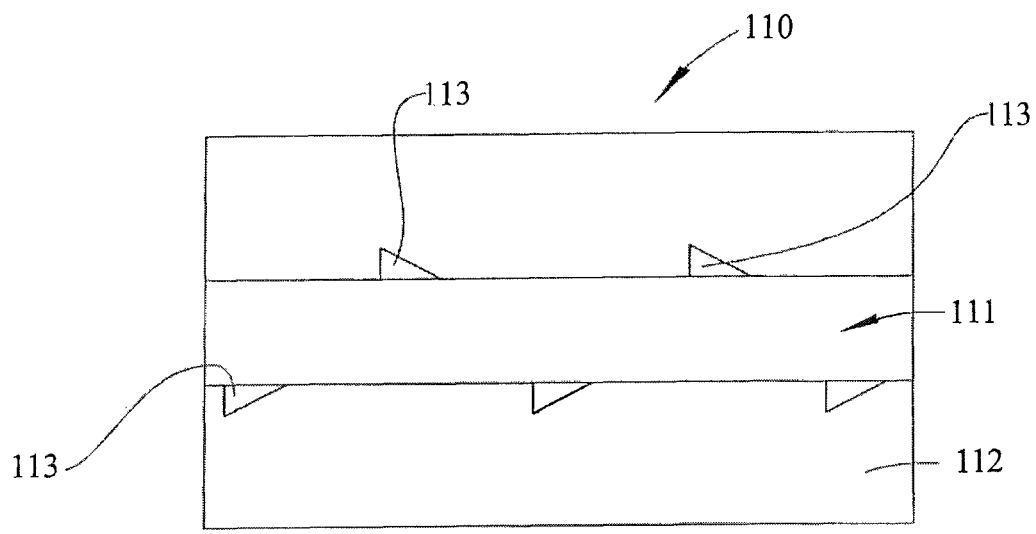
FIG. 4A is a front side view of a first nest half of the barbed suture forming nest of FIG. 3.
Figure 4B:
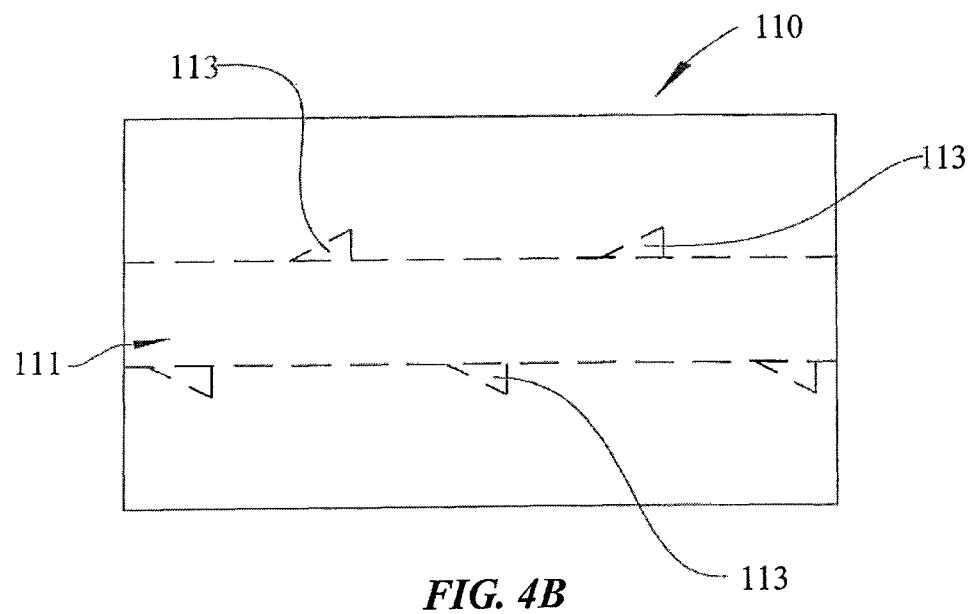
FIG. 4B is a back side view of the first nest half of FIG. 4A.
Figure 5A:
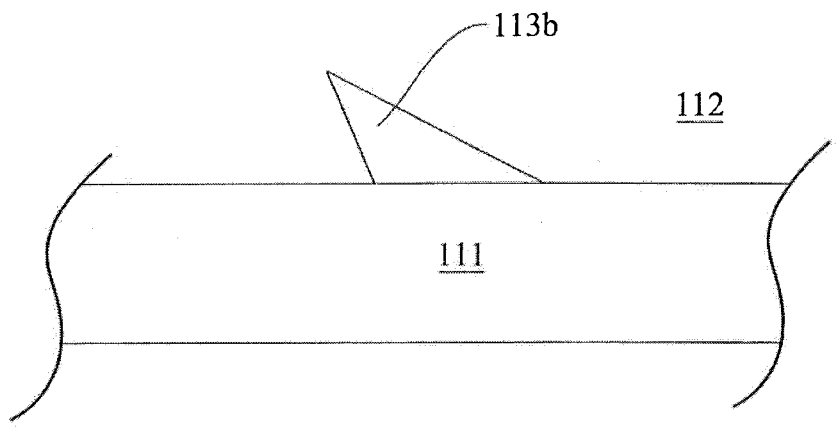
FIGS. 5A and 5B are enlarged sectional views of nest halves according to alternative embodiments of the present disclosure.
Figure 5B:
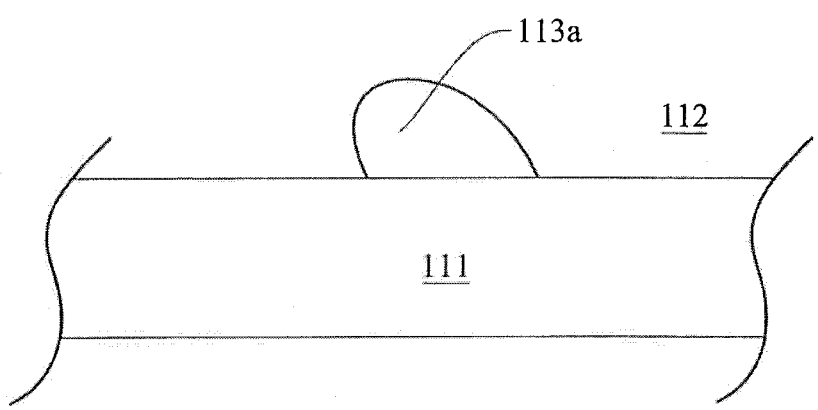

With reference now to FIGS. 3, 4A and 4B, first nest half 110 of suture forming nest 100 defines a longitudinal groove 111 along an inner surface 112. Longitudinal groove 111 is configured to receive elongate body 12 of suture 10. A plurality of barb-shaped recesses 113 are formed in inner surface 112 along the length of longitudinal groove 111. As shown, recesses 113 are formed along first and second sides of groove 111 in an alternating pattern. It is envisioned, however, that recesses 113 may be formed in inner surface 112 along only one side of groove 111. It is further envisioned that first nest half 110 may include only a single recess 113 formed in inner surface 112. As shown, recesses 113 form substantially triangular cut-outs. Turning briefly to FIGS. 5A and 5B, first nest half 110 may instead define sharpened recesses 113a (FIG. 5A) for forming a pointed barb or rounded recesses 113b (FIG. 5B) for forming a smooth barb. In one embodiment, nest half 110 may define recesses 113 having one or more different configurations. In another embodiment, recesses 113 may not only differ in shape, but also in size.

Figure 6A:
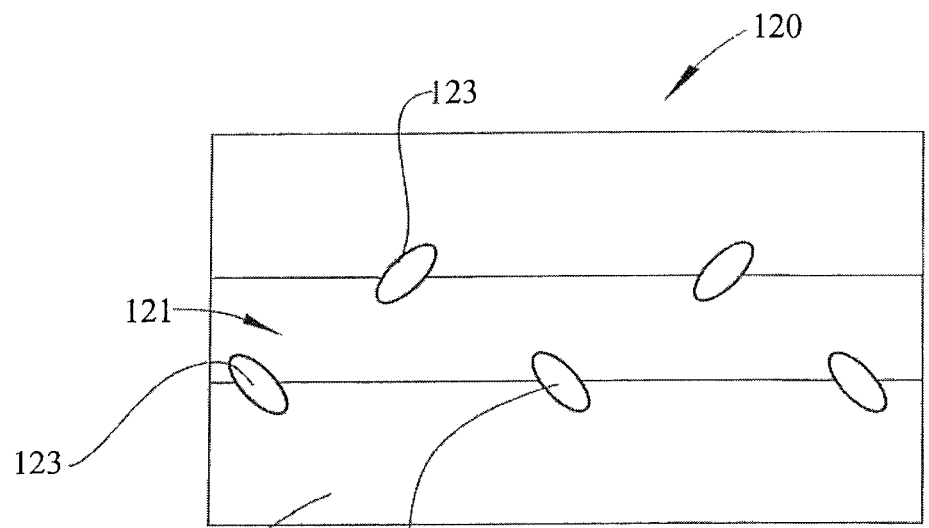
FIG. 6A is a front side view of a second nest half of the barbed suture forming nest of FIG. 3.
Figure 6B:
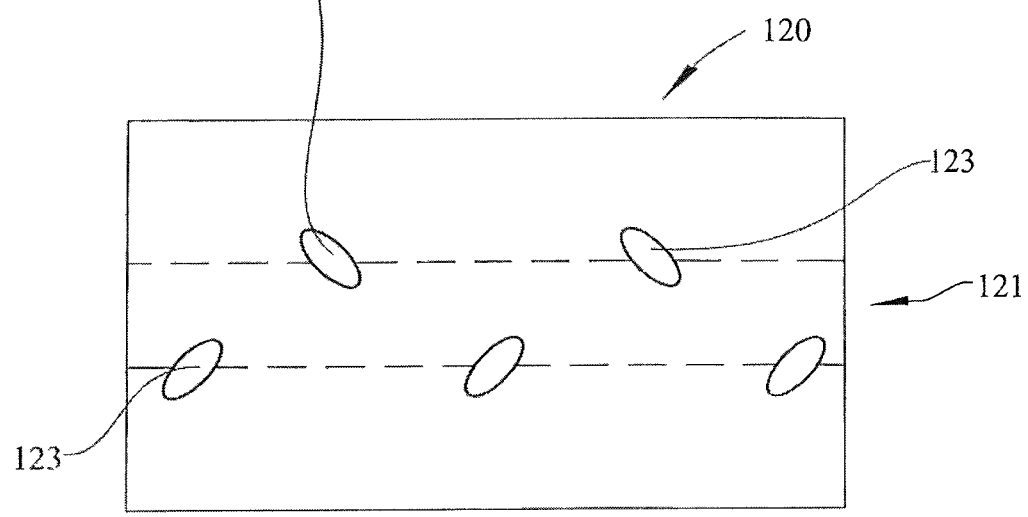
FIG. 6B is a back side view of the second nest halve of FIG. 6A.
Figure 8:
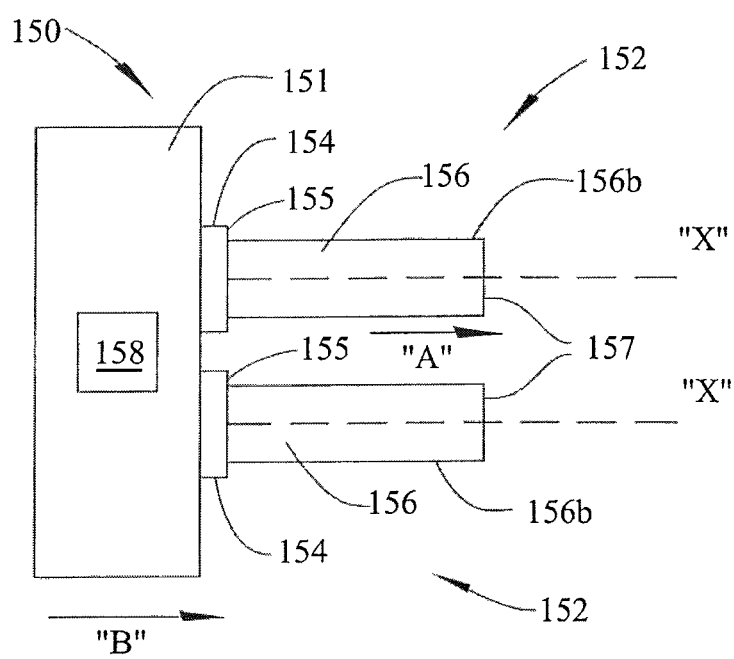
FIG. 8 is a side view of the punch of FIG. 7.

With reference now to FIGS. 3, 6A and 6B, second nest half 120 defines a longitudinal groove 121 along an inner surface 122 thereof. Longitudinal groove 121 is configured to receive elongate body 12 of suture 10 and corresponds to longitudinal groove 111 of first nest half 110. Longitudinal grooves 111, 121 cooperate when inner surfaces 112, 122 of respective first and second halves 110, 120 are in contact with each other to form passage 101 through barb forming nest 100. Second nest half 120 further defines a plurality of openings 123. Openings 123 extend through second nest half 120. Each opening 123 correspond to a recess 113 formed in first nest half 110. Each of openings 123 is configured to receive a distal end of a punch member 156 (FIG. 8). As will be discussed in further detail below, punch member 156 is received through openings 123 to form barb 14 in elongate body 12 of suture 10 (FIG. 1). As shown, openings 123 define slots having a substantially oval cross-section configured to receive a distal end 156b of punch member 156 having a substantially oval cross-section. Openings 123 are oriented such that a portion of distal end 156b of punch member 156 engages a portion of elongate body 12 of suture 10.

Figure 7:
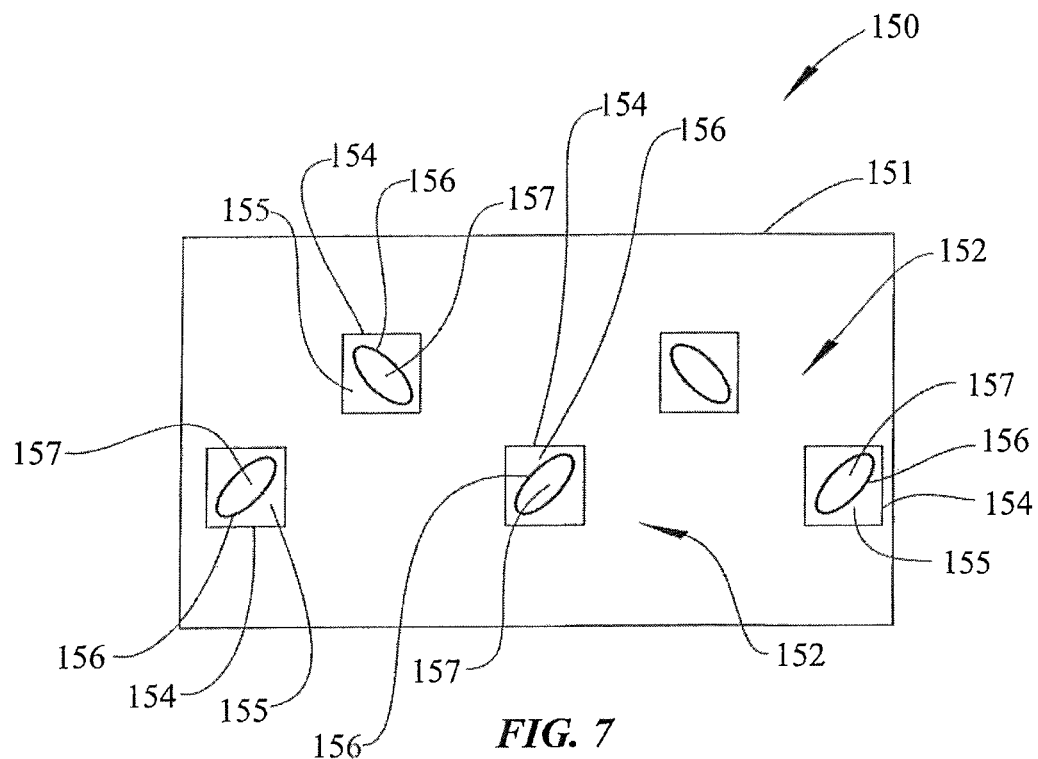
FIG. 7 is a front view of a punch for use with the barbed suture forming nest of FIG. 3.

With reference to FIGS. 7 and 8, an apparatus for use with suture forming nest 100 is shown generally as punch 150. Punch 150 includes a base 151 and a plurality of punch assemblies 152 operably connected to base 151. The configuration of punch assemblies 152 corresponds to openings 123 of suture forming nest 100. Punch assemblies 152 each include a base 154 and a punch member 156 extending from base 154. Punch member 156 includes a rounded distal end 156b. Although shown having a substantially orthogonal distal surface 157, it is envisioned that distal surface 157 of punch member 156 may be angled. Angling of distal surface 157 may facilitate movement of the suture material during forming of barbs 14 and/or may facilitate the forming of recess 15 (FIG. 1A) on elongate body 12 of suture 10. Although not shown, distal surface 157 of punch member 156 may be contoured or otherwise configured to facilitate forming of one or more ridges 15 on elongate body 12 of suture 10. Punch member 156 is of sufficient length to extend through openings 123 of second nest half 120 such that distal end 156b of punch member 156 engages elongate body 12 of suture 10. In one embodiment, punch member 156 is of a length such that a distal surface 155 of base 154 engages an outer surface of second nest half 120. In this manner, distal surface 155 of base 154 acts as a stop to prevent over insertion of punch member 156 within opening 123.

Base members 154 and/or punch members 156 may be configured for selective rotation about a longitudinal axis "X" thereof (FIG. 8). In this manner, punch members 156 may be reoriented to correspond with alternatively oriented openings in alternative suture forming nests. Base members 154 may also be configured for selective removal from punch 150. In this manner, one or more punch assemblies 152 may be removed such that punch 150 may be used with a suture forming nest having fewer than five (5) openings. Additionally, selective removal of base members 154 permits replacing punch members 156 in the event of damage to punch member 156, or to replace punch members 156 with alternatively configured punch members (not shown) for use with alternatively formed openings.

With reference still to FIGS. 7 and 8, in one embodiment, base members 154 are configured to selectively extend from base 151 of punch 150. In this manner, punch 150 may be fixed relative to suture forming nest 100 and positioned such that punch members 156 align with openings 123 in second nest half 110. Upon advancement of base members 154 relative to base 151, as indicated by arrows "A" (FIG. 8), punch members 156 are received in openings 123 (FIG. 6A) of second nest half 120. Alternatively, base members 154 may be fixed relative to base 151, while base 151 is configured to be moved relative to suture forming nest 100. In this manner, upon advancement of base 151 relative to nest 100, as indicated by arrows "B" (FIG. 8), punch members 156 are received in openings 123 of second nest half 120. Regardless of whether either or both of base 151 and/or base members 154 are advanced, retraction of respective base members 154 and/or base 151, causes retraction of punch members 156 from within openings 123 of second nest half 120.

Still referring to FIGS. 7 and 8, base 151 of punch 150 includes a mechanism 158 for heating each of punch members 156. Mechanism 158 may include a heating element (not shown) or any other suitable method for heating punch member 156, i.e., laser beams, electric current flowing through resistors, inductive heating. Alternatively, base 151 may include an ultrasonic device (not shown) for ultrasonically oscillating punch members 156. In certain embodiments, the ultrasonic device creates friction between elongate body 12 of suture 10 (FIG. 1A) and punch member 156, thereby causing that portion of elongate body 12 in contact with punch member 156 to soften or become pliable. In yet other embodiments, punch members 156 and/or elongate body 12 may be treated with a solvent or other chemical to soften or make pliable the material forming elongate body 12 in order to facilitate molding of barbs 14.

Figure 9:
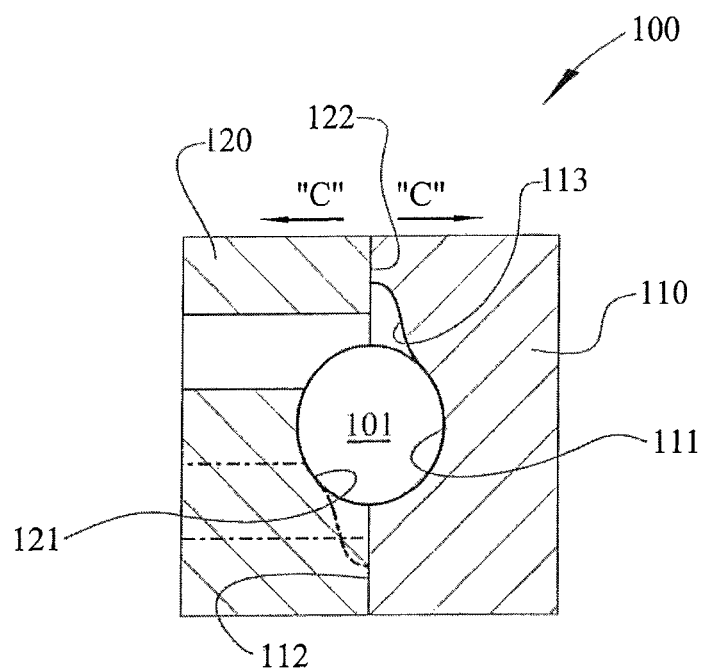
FIG. 9 is a cross-sectional view of the barbed suture forming nest of FIG. 3 taken along plane 9 of FIG. 3.
Figure 10:
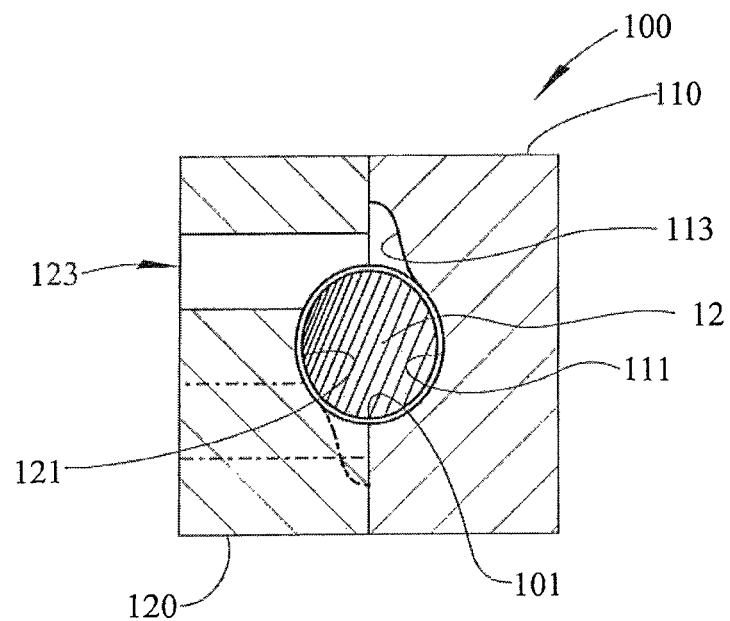
FIG. 10 is a cross-sectional view of the barbed suture forming nest of FIG. 9, including a length of suture received therein.

The use of suture forming nest 100 will now be described with reference to FIGS. 9-12. Referring initially to FIG. 9, inner surfaces 112, 122 of first and second nest halves 110, 120 are shown in contact to form elongated passage 101. A suture 10 may then be loaded through longitudinal passage 101. Alternatively, either or both of first and second nest halves 110, 120 may be approximated away from the other nest half, as indicated by arrows "C", such that a suture may be loaded therein. Turning briefly to FIG. 10, suture 10 is shown positioned within passage 101 of suture nest 100.

Figure 11:
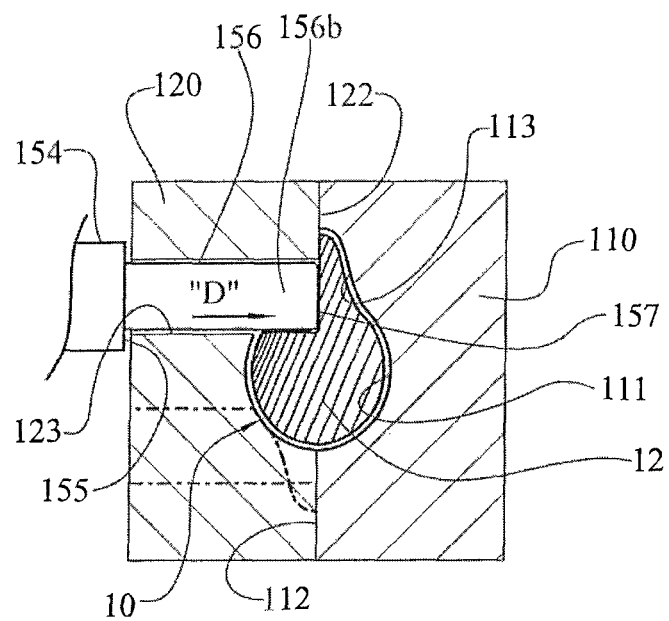
FIG. 11 is a cross-sectional view of the barbed suture forming nest and suture of FIG. 10, including a punch assembly being operably engaged therewith.

With reference now to FIG. 11, once suture 10 is positioned within elongate passage 101 of barb forming nest 100, punch 150 (FIG. 7) are activated and punch members 156 thereof are inserted through corresponding openings 123 in second nest half 120 of nest 100. Punch members 156 may be inserted into openings 123 individually or simultaneously. As discussed above, punch 150 includes a plurality of punch members 156 corresponding in size and location with openings 123 of second nest half 120.

With reference still to FIG. 11, as discussed above, punch member 156 is advanced, as indicated by arrow "D", such that distal end 156b thereof engages a portion of elongate body 12 of suture 10. Continued advancement of punch member 156 relative to suture 10 causes localized softening or melting of elongate body 12 of suture 10 and displacement of the softened/melted material into recess 113 of first nest half 110. As discussed above, distal surface 157 of punch member 156 may be angled to facilitate flow of the melted material into recess 113. In one embodiment, and as shown, distal surface 155 of base member 154 is configured to engage second nest half 120 of suture forming nest 100 upon complete reception of punch member 156 within opening 123, thereby acting as a stop to prevent over-insertion of punch members 156 into openings 123. Alternatively, the mechanism for advancing and retracting either or both of base members 154 and base 151 may include a stop feature to prevent over-insertion of punch members 156 within openings 123.

Figure 12:
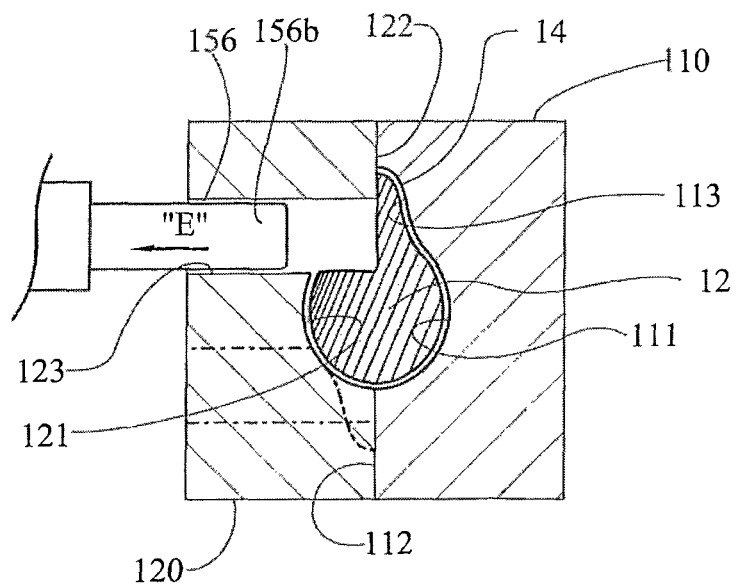
FIG. 12 is a cross-sectional view of the barbed suture forming nest and suture of FIG. 11, including the punch assembly being operably disengaged therewith.

Once punch member 156 has been appropriately advanced, heating mechanism 158 may be deactivated to permit cooling of punch member 156. In one embodiment, punch assemblies 152 include a heat sink (not shown) for assisting in cooling punch member 156. With reference now to FIG. 12, upon sufficient cooling of punch member 156, punch member 156 is retracted away from elongate body 12 of suture 10, as indicated by arrow "E", such that distal end 156b of punch member 156 disengages from elongate body 12 of suture 10.

Depending on the configuration of suture forming nest 100 and the desired number and configuration of barbs 14, suture 10 may be advance longitudinally relative to suture forming nest 100 to receive a smooth length of suture 10 therein. Suture 10 may also be rotated along the longitudinal axis to radially offset the subsequently formed barbs from the previously formed barbs. Alternatively, suture forming nest 100 may be configured to accommodate an entire length of suture 10 such that barbs 14 may be formed simultaneously or without moving suture 10. In another embodiment, suture 10 is removed from within elongate passage 101 of nest 100 and rotated one-hundred eighty degrees (180°) to form barbs extending opposite the first barbs. In this manner, a bi-directional barbed suture may be formed. The barb forming process may be repeated along the length of suture 10.

It is envisioned that suture forming nest 100 may be modified to form barbs of various configuration. Barbs 14 may be arranged in any suitable pattern, for example, helical, linear, or randomly spaced. The pattern may be symmetrical or asymmetrical. The number, configuration, spacing and surface area of barbs 14 may vary depending upon the tissue in which the suture is used, as well as the composition and geometry of the material utilized to form suture 10. Additionally, the proportions of barbs 14 may remain relatively constant while the overall length of barbs 14 and the spacing of barbs 14 may be determined by the tissue being connected. For example, if suture 10 is to be used to connect the edges of a wound in skin or tendon, barbs 14 may be made relatively short and more rigid to facilitate entry into this rather firm tissue. Alternatively, if suture 10 is intended for use in fatty tissue, which is relatively soft, barbs 14 may be made longer and spaced further apart to increase the ability of the suture to grip the soft tissue.

The surface area of barbs 14 may also vary. For example, fuller-tipped barbs may be made of varying sizes designed for specific surgical applications. For joining fat and relatively soft tissues, larger barbs may be desired, whereas smaller barbs may be more suitable for collagen-dense tissues. In some embodiments, a combination of large and small barbs within the same structure may be beneficial, for example, when a suture is used in tissue repair with differing layer structures. The use of the combination of large and small barbs with the same suture wherein the barb sizes are customized for each tissue layer may maximize the anchoring properties of the suture. In particular embodiments, a single directional suture may have both large and small barbs; in other embodiments a bi-directional suture may have both large and small barbs. The barbs formed may include geometrical shapes such as round, triangular, square, oblique, elliptical, octagonal, rectangular, and flat.

Figure 13:
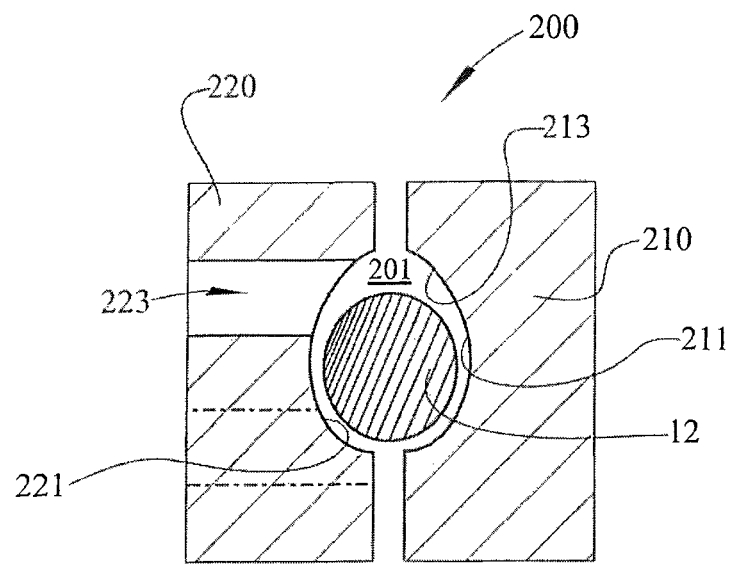
FIG. 13 is a cross-sectional view of a barbed suture forming nest according to an alternative embodiment of the present disclosure, in an open position and including a length of suture received therethrough.
Figure 14:
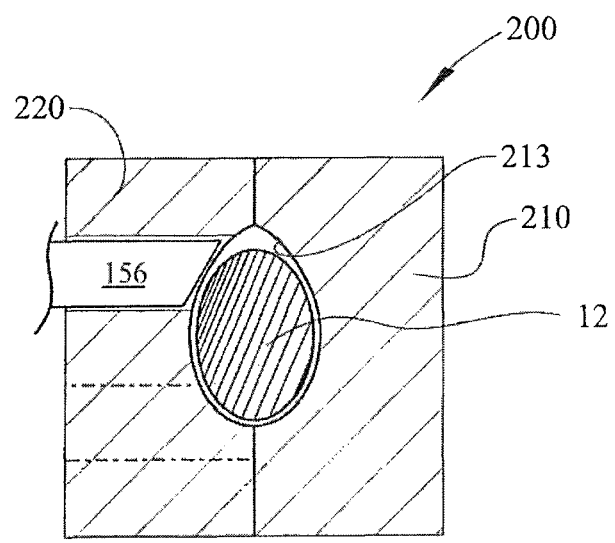
FIG. 14 is a cross-sectional view of the barbed suture forming nest of FIG. 13, in a closed position.

With reference now to FIGS. 13 and 14, an alternative embodiment of an apparatus for forming barbs 14 on suture 10 (FIGS. 1A and 1B) is shown generally as suture forming nest 200. Suture forming nest 200 is substantially similar to suture forming nest 100 described hereinabove, and therefore will only be described as relates to the differences therebetween.

Still referring to FIGS. 13 and 14, suture forming nest 200 includes a first nest half 210 defining a longitudinal groove 211 and a second nest half 202 defining a longitudinal groove 221. First and second nest halves 210, 220 correspond to form elongate passage 201. As seen in FIG. 13, elongate passage 201 is configured to receive elongate body 12 of suture 10 having a diameter that is larger than the diameter of elongate passage 201. Alternatively, elongate body 12 of suture 10 may have a different cross-sectional configuration than the cross-sectional configuration of elongate passage 201. As shown, elongate body 12 of suture 10 includes a substantially circular cross-sectional configuration while elongate passage 201 includes a substantially oval cross-sectional configuration. Although shown having a substantially oval cross-sectional configuration, it is envisioned that elongate passage 201 may have other cross-sectional shapes. For example, elongate passage 201 may instead have a diamond-shaped cross-sectional configuration. First nest half 210 further defines at least one recess 213 for forming a barb 14 on suture 10 (FIG. 1A). Second nest half 220 further defines at least one opening 223 corresponding to barb forming recess 213. As with opening 123 of second nest half 120, opening 223 is configured to receive punch member 156.

Turning to FIG. 14, first and second nest halves 210, 220 are configured such that, when suture forming nest 200 is closed about elongate body 12 of suture 10, elongate body 12 is deformed in a manner that pinches a portion of elongate body 12 towards recess 213. In this manner, first and second nest halves 210, 220 facilitate the forming of a barb 14 on elongate body 12 of suture 10.

Figure 15:
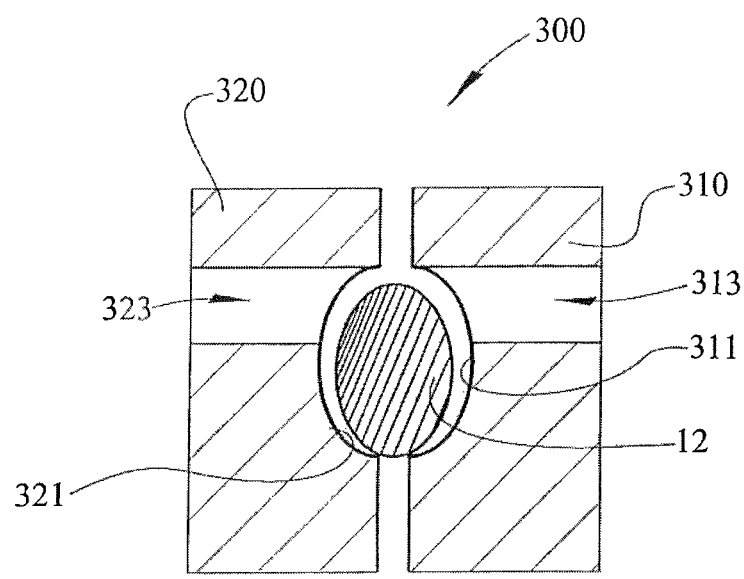
FIG. 15 is a cross-sectional view of a barbed suture forming nest according to another embodiment of the present disclosure, in an open position and including a length of suture received therethrough.
Figure 16:
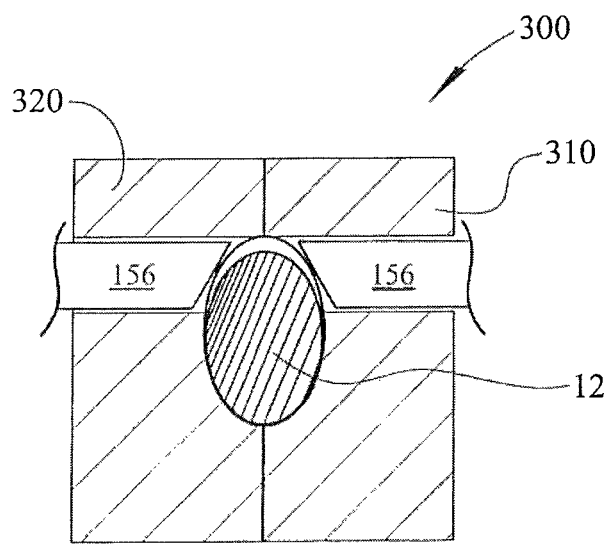
FIG. 16 is a cross-sectional view of the barbed suture forming nest of FIG. 15, in a closed position, including a pair of punch assemblies operably engaged therewith.

With reference now to FIGS. 15 and 16, another embodiment of an apparatus for forming barbs on elongate body 12 of a suture is shown generally as suture forming nest 300. Suture forming nest 300 is substantially similar to suture forming nests 100 and 200 described hereinabove, and therefore, will only be described as relates to the differences therebetween.

Suture forming nest 300 includes first and second nest halves 310, 320. Each of first and second nest halves 310, 320 define a longitudinal groove 311, 321, respectively, which correspond to form an elongate passage 301. Each of first and second nest halves 310, 320 further define openings 313, 323, respectively. Openings 313, 323 are aligned with one another and are each configured to receive a punch member 156. As seen in FIG. 16, first and second nest halves 310, 320 are configured to simultaneously receive punch members 156 through respective openings 313, 323 to cause the formation of a barb on elongate body 12 of the suture.

Figure 17:
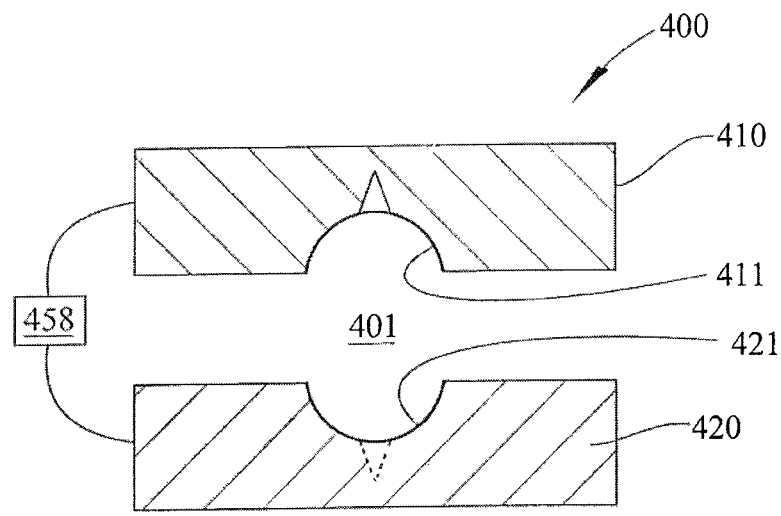
FIG. 17 is a cross-sectional view of a barb forming nest according to yet another embodiment of the present disclosure.
Figure 18:
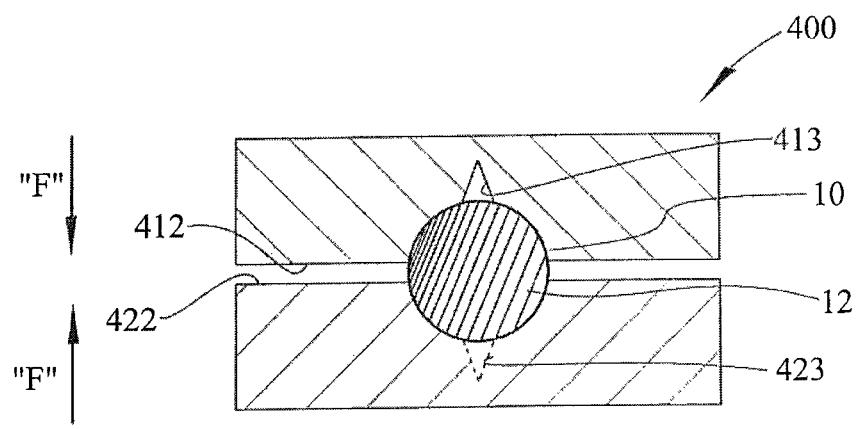
FIG. 18 is a cross-sectional view of the barb forming nest of FIG. 17 including a suture received therein and prior to barb formation.
Figure 19:
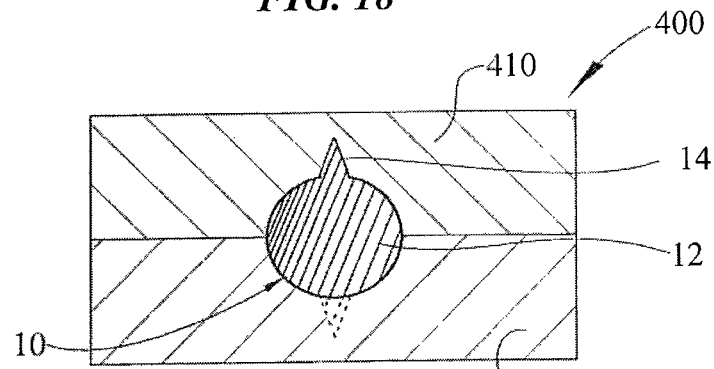
FIG. 19 is a cross-sectional view of the barb forming nest and suture of FIG. 17, post barb formation.

With reference now to FIGS. 17-19, yet another embodiment of a suture forming nest according to the present disclosure is shown generally as suture forming nest 400. Barb forming nest 400 is similar to suture forming nests 100, 200 and 300 described hereinabove, and therefore, will only be described as relates to the differences therebetween.

With reference still to FIGS. 17-19, suture forming nest 200 includes first and second nest halves 410, 420. Each of barb forming nests 410, 420 include an inner surface 412, 422 defining a longitudinal groove 411, 421, respectively. Longitudinal grooves 411, 421 cooperate to form an elongate passage 401 between first and second nest halves 410, 420 when inner surfaces 412, 422 thereof are in contact. First nest half 410 further defines at least one recess 413 extending from longitudinal groove 411. As shown, recess 413 extends perpendicular to inner surface 412 to form a barb 14 (FIG. 19) that extends perpendicular to elongate body 12 of suture 10, however, it is envisioned that recess 413 may instead extend from longitudinal groove 411 at various angles so as to form a barb 14 extending from elongate body 12 of suture 10 at various angles. It is further envisioned that second nest half 420 may also include one or more recesses 423 (shown in phantom) for forming one or more barbs 14. Either or both of first and second nest halves 410, 420 are operably connected to a heating mechanism 458 for selectively heating at least portions of first and second nest halves 410, 420. In one embodiment, heating mechanism 458 heats only the portions of first and second nest halves 410, 420 corresponding to recesses 423.

The use of barb forming nest 400 will be now described with particular reference to FIGS. 17-19. Initially, a length of suture 10 is loaded within elongated passage 401 of nest 400. As seen, suture 10 includes a diameter larger then the diameter of elongated passage 401. Heating mechanism 458 is then activated to heat either or both of first and second nest halves 410, 420. Heating of nest halves 410, 420 causes suture 10 to soften and/or melt. Approximation of first and second nest halves 410, 420 towards each other, as indicated by arrows "F" (FIG. 18), as suture 10 is melted, forces the melted material of suture 10 into recess 413 to form barb 14. Once inner surfaces 412, 422 of first and second nest halves 410, 420 are in contact, heating mechanism 458 is deactivated and suture 10 is permitted to solidify. As with punch member 156, first and second nest halves 410, 420 may include a heat sink (not shown) to facilitate cooling of suture 10. Once suture 10 has cooled sufficiently, first and second nest halves 410, 420 are approximated away from each other and suture 10 is removed. Suture 10 may then be repositioned within nest 400 and the process may be repeated. As with the previously disclosed suture forming nests, it is envisioned that barb forming nest 400 may be configured to form barbs 14 along an entire length of elongate body 12 of suture 10 simultaneously.

While the above description contains many specifics, these specifics should not be construed as limitations on the scope of the disclosure, but merely as exemplifications of embodiments thereof. Those skilled in the art will envision many other possibilities within the scope and spirit of the disclosure as defined by the claims appended hereto. For example, each of first and second nest halves 110, 120 may each include both openings and recesses. In this manner, radially offset barbs may be formed without moving suture 10 relative to the nest. A second punch may also be used with the nest to simultaneously form the second set of barbs. Alternatively, or in addition, openings and recesses may be formed in either or both of the top and bottom surfaces of the nest halves to further permit forming of radially offset barbs without moving suture 10.

The invention claimed is:

1. A method of making a barbed suture, the method comprising:
   providing a suture nest and a punch apparatus including at least one punch member, wherein the punch apparatus is configured for operable engagement with the suture nest and the suture nest defines at least one opening corresponding to the at least one punch member and at least one recess opposite the at least one opening;
   loading a suture through the suture nest;
   heating the at least one punch member;
   engaging a distal surface of the at least one punch member with the suture by receiving the at least one punch member through the at least one opening in the suture nest to displace a portion of the suture into the at least one recess to form a displaced portion of suture, wherein the displaced portion of suture remains integral with the suture; and
   disengaging the punch member from the suture.

2. The method of claim 1, wherein the suture nest includes first and second suture nest halves.

3. The method of claim 2, wherein the first suture nest half defines a first longitudinal groove.

4. The method of claim 3, wherein the first suture nest half defines the at least one recess, the at least one recess being formed along the first longitudinal groove.

5. The method of claim 4, wherein the second suture nest half defines a second longitudinal groove corresponding to the first longitudinal groove.

6. The method of claim 5, wherein the second suture nest half defines the at least one opening corresponding to the at least one recess of the first suture nest half.

7. The method of claim 5, wherein the first and second longitudinal grooves form an elongate passage through the suture nest when the first and second suture nest halves are engaged.

8. The method of claim 1, further including cooling the at least one punch member prior to disengaging the distal surface of the punch member from the suture.

9. The method of claim 1, further including advancing the suture longitudinally relative to the suture nest.

10. The method of claim 9, further including reengaging the distal surface of the punch member with the suture.

11. The method of claim 1, further including rotating the suture along a longitudinal axis.

12. The method of claim 1, wherein engaging the distal surface of the at least one punch member with the suture includes maintaining the distal surface with the suture until disengaging the punch member from the suture.

13. The method of claim 1, wherein the distal surface of the at least one punch member is rounded.

14. The method of claim 1, wherein engaging the distal surface of the at least one punch member with the suture includes moving the punch member perpendicular to the suture.

15. A barbed suture formed by the method of claim 1.

16. A method of making a barbed suture, the method comprising:
 advancing at least one punch member through an opening in a suture nest into contact with a suture positioned in the suture nest, the suture nest having a recess adjacent to the suture positioned therein opposite the opening, wherein contact of the punch member with the suture causes displacement of a portion of the suture into the recess in the suture nest, the displaced portion of the suture remaining integral with the suture and forming a barb; and
 withdrawing the at least one punch member from contact with the suture.

17. The method of claim 16, further including advancing the suture longitudinally relative to the suture nest and repeating the advancing and withdrawing steps.

18. The method of claim 16, further including rotating the suture along a longitudinal axis and repeating the advancing and withdrawing steps.

19. The method of claim 16, further including heating the at least one punch member.

20. The method of claim 16, further including ultrasonically oscillating the at least one punch member.

21. The method of claim 16, wherein advancing the at least one punch member into contact with the suture includes contacting the suture with a distal surface of the at least one punch member.

22. The method of claim 16, wherein advancing the at least one punch member into contact with the suture includes moving the punch member perpendicular to the suture.

* * * * *